United States Patent
Burbidge et al.

(10) Patent No.: US 11,992,035 B2
(45) Date of Patent: *May 28, 2024

(54) COHESIVE THIN LIQUIDS TO PROMOTE SAFE SWALLOWING IN DYSPHAGIC PATIENTS

(71) Applicant: Société des Produits Nestlé S.A., Vevey (CH)

(72) Inventors: Adam Stewart Burbidge, Arzier (CH); Jan Engmann, Epalinges (CH); Simina Popa Nita, Morges (CH)

(73) Assignee: Societe des Produits Nestle S.A., Vevey (CH)

( * ) Notice: Subject to any disclaimer, the term of this patent is extended or adjusted under 35 U.S.C. 154(b) by 290 days.

This patent is subject to a terminal disclaimer.

(21) Appl. No.: 16/790,286

(22) Filed: Feb. 13, 2020

(65) Prior Publication Data

US 2020/0196651 A1    Jun. 25, 2020

Related U.S. Application Data

(63) Continuation of application No. 14/365,731, filed as application No. PCT/EP2012/075697 on Dec. 17, 2012, now Pat. No. 10,582,722.

(60) Provisional application No. 61/570,888, filed on Dec. 15, 2011.

(30) Foreign Application Priority Data

Dec. 15, 2011 (EP) .................... 11193799

(51) Int. Cl.
| | |
|---|---|
| *A61K 36/185* | (2006.01) |
| *A23L 29/20* | (2016.01) |
| *A23L 29/206* | (2016.01) |
| *A23L 29/238* | (2016.01) |
| *A23L 29/256* | (2016.01) |
| *A23L 29/269* | (2016.01) |
| *A23L 33/10* | (2016.01) |
| *A23L 33/105* | (2016.01) |
| *A23L 33/115* | (2016.01) |
| *A23L 33/135* | (2016.01) |
| *A23L 33/15* | (2016.01) |
| *A23L 33/175* | (2016.01) |
| *A23L 33/21* | (2016.01) |
| *A61K 31/715* | (2006.01) |

(52) U.S. Cl.
CPC ............. *A23L 29/271* (2016.08); *A23L 29/20* (2016.08); *A23L 29/206* (2016.08); *A23L 29/238* (2016.08); *A23L 29/256* (2016.08); *A23L 29/27* (2016.08); *A23L 29/272* (2016.08); *A23L 33/10* (2016.08); *A23L 33/105* (2016.08); *A23L 33/115* (2016.08); *A23L 33/135* (2016.08); *A23L 33/15* (2016.08); *A23L 33/175* (2016.08); *A23L 33/21* (2016.08); *A61K 31/715* (2013.01); *A61K 36/185* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,664,847 A | 5/1972 | Hyldon et al. | |
| 6,271,001 B1 | 8/2001 | Clarke et al. | |
| 6,277,395 B1 | 8/2001 | Fukui et al. | |
| 7,008,654 B1 | 3/2006 | Fuchs et al. | |
| 7,115,297 B2 | 10/2006 | Stillman | |
| 2004/0258823 A1 | 12/2004 | Dufresne et al. | |
| 2007/0224126 A1 | 9/2007 | Dufresne et al. | |
| 2009/0074940 A1 | 3/2009 | Sliwinski | |

FOREIGN PATENT DOCUMENTS

| | | |
|---|---|---|
| CN | 1553816 | 12/2004 |
| EP | 3360428 A1 | 8/2018 |
| JP | 2000041594 | 2/2000 |
| JP | 2000191553 | 7/2000 |
| JP | 2003189802 A | 7/2003 |
| JP | 2005187362 | 7/2005 |
| JP | 2006516995 | 7/2006 |
| JP | 2008228729 A | 10/2008 |
| JP | 2009256216 A | 11/2009 |
| WO | WO03011051 | 2/2003 |
| WO | WO2007097315 | 8/2007 |
| WO | 2010050541 | 5/2010 |

(Continued)

OTHER PUBLICATIONS

Chan et al. "Study of the shear and extensional rheology of casein, waxy maize starch and their mixtures." Food Hydrocolloids 21 (5): 716-725, 2007 (Year: 2007).*
International Search Report for International Application No. PCT/EP2012/075697 dated Mar. 13, 2013.
International Written Opinion for International Application No. PCT/EP2012/075697 dated Mar. 13, 2013.
T. Funami et al., "Texture design for products using food hydrocolloids," Food Hydrocolloids, vol. 26, No. 2, Feb. 17, 2011, pp. 412-420, XP028288966.
S. Ishihara et al., "Swallowing profiles of food polysaccharide gels in relation to bolus rheology," Food Hydrocolloids, vol. 25, No. 5, Sep. 24, 2010, pp. 1016-1024, XP028163244.

(Continued)

*Primary Examiner* — Emily A Cordas
(74) *Attorney, Agent, or Firm* — K&L Gates LLP

(57) ABSTRACT

Nutritional products having improved cohesiveness for promoting safer swallowing of food boluses for patients having swallowing conditions are provided as well as methods of making and using such products. The nutritional products may include nutritional compositions and high molecular weight, water-soluble polymers such that the nutritional products have extensional viscosities that provide improved cohesiveness to the nutritional products. Methods of administering such nutritional products to patients having impaired swallowing ability and/or dysphagia are also provided.

7 Claims, No Drawings

(56) References Cited

FOREIGN PATENT DOCUMENTS

| WO | WO2010122332 | 10/2010 |
|----|--------------|---------|
| WO | 2011056487 | 5/2011 |
| WO | 2011112087 A1 | 9/2011 |
| WO | WO2012117065 | 9/2012 |

OTHER PUBLICATIONS

Ramsden Chapter 15 "Plant and Algal Gums and Mucilages." Chemical and Functional Properties of Food Saccharides, edited by Piotr Tomasik: 231, 2003 (Year: 2003).
Gull-Guerrero "Nutritional composition of Plantago species (P. major L., P. lanceolata L., and P. media L.)." Ecology of Food and Nutrition 40(5): 481-495, 2001 (Year: 2001).
Cardenas et al. "Rheology and aggregation of cactus (Opuntia ficus-indica) mucilage in solution", Journal of the Professional Association for Cactus Development 2: 152-159, 1997 (Year: 1997).
Japanese Office Action for Application No. P2014-54651, Distpach No. 460559, Dispatch Date Oct. 11, 2016, 10 pages.
Chinese Office Action for Application No. 201280069746.7, dated Jun. 29, 2016, 21 pages.
Ghadimi et al. "Free amino acids of different kinds of milk", American Journal of Clinical Nutrition 13 (1963): 75-81, 1963.
Gronlund et al. "Maternal breast- milk and intestinal bifidobacteria guide the compositional development of the Bifidobacterium microbiota in infants at risk of allergic disease." Clinical & Experimental Allergy 37(12): 1764-1772, 2007.
De Block et al. "Evaluation of two methods for the determination of lactulose in milk." International Dairy Journal 6(2): 217-222, 1996.
Sengkhamparn et al. "Physicochemical properties of pectins from okra (Abelmoschus esculentus (L.) Moench)", Food Hydrocolloids (1 ): 35-41 Jan. 2010.
Redgwell et al., "Structural features of the mucilage from the stem pith of kiwifruit (Actinidia deliciosa): part I, structure of the inner core", Carbohydrate Research 153 (1):97-106, 1986.
Canada Patent Office Communication for Application No. 2,858,636, dated Feb. 5, 2021, 3 pages.
Priority Document of EP Application No. 11193799.1, Filed on Dec. 15, 2011, 46 Pages.
Priority Document of U.S. Appl. No. 61/570,888, filed Dec. 15, 2011, 52 Pages.
Nishinari et al., "Role of Fluid Cohesiveness in Safe Swallowing", Science of Food, vol. 3, Issue No. 5, 2019, pp. 1-13.
Tashiro et al., "Relationship between the Rheological Properties of Thickener Solutions and their Velocity through the Pharynx as Measured by the Ultrasonic Pulse Doppler Method", Bioscience, Biotechnology and Biochemistry, vol. 74, Issue No. 8, 2010, pp. 1598-1605.
Kumagai et al., "Relationship between Flow Properties of Thickener Solutions and their Velocity through the Pharynx Measured by the Ultrasonic Pulse Doppler Method", Food Science and Technology Research, vol. 15, Issue No. 3, 2009, pp. 203-210.
Duxenneuner et al., "Extensional Properties of Hydroxypropyl Ether Guar Gum Solutions", Biomacromolecules, vol. 9, Issue No. 11, 2008, pp. 2989-2996.
Bourbon et al., "Characterization of Galactomannans Extracted from Seeds of Gleditsia Riacanthos and Sophora Japonica through Shear and Extensional Rheology: Comparison with Guar Gum and Locust Bean Gum", Food Hydrocolloids, vol. 24, Issue No. 2-3, 2010, pp. 184-192.
Nishinari et al., "Effect of shear Thinning on Aspiration-Towards making Solutions for Judging the Risk of Aspiration", Food Hydrocolloids, vol. 25, Issue No. 7, 2011, pp. 1737-1743.
Newman et al., "Effect of Bolus Viscosity on the Safety and Efficacy of Swallowing and the Kinematics of the Swallow Response in Patients With Oropharyngeal Dysphagia: White Paper by the European Society for Swallowing Disorders (Essd)", Dysphagia, vol. 31, Issue No. 2, 2016, 18 Pages.

Steele et al., "The Influence of Food Texture and Liquid Consistency Modification on Swallowing Physiology and Function: a Systematic Review", Dysphagia, vol. 30, Issue No. 1, 2015, 25 Pages.
McKinley, "Visco-Elasto-Capillary Thinning and Break-up of Complex Fluids", Hatsopoulos Microfluids Laboratory, Report No. 05-P-04, 2005, pp. 1-49.
Gallegos et al., "Rheology and Dysphagia: an overview", Annual Transactions of the Nordic Rheology Society, vol. 20, 2012, pp. 3-10.
Garcia et al., "Viscosity Measurements of Nectar- and Honey-Thick Liquids: Product, Liquid, and Time Comparisons", Dysphagia, vol. 20, Issue No. 4, 2005, pp. 325-335.
Chang et al., "Rheological Properties of Six Plant-Based Seed Gums", American Journal of Analytical Chemistry, vol. 8, Issue No. 11, 2017, pp. 690-707.
Sopade et al., "Rheological Characterisation of Food Thickeners Marketed in Australia in Various Media for the Management of Dysphagia. I: Water and Cordial", Journal of Food Engineering, vol. 79, Issue No. 1, 2007, pp. 69-82.
Sopade et al., "Rheological Characterisation of Food Thickeners Marketed in Australia in Various Media for the Management of Dysphagia. III: Fruit Juice as Dispersing Medium", Journal of Food Engineering, vol. 86, Issue No. 4, 2008, pp. 604-615.
Srichamroen, "Influence of Temperature and Salt on Viscosity Property of Guar Gum", Naresuan University Journal, vol. 15, Issue No. 2, 2007, pp. 55-62.
European Patent Office Communication for Application No. 18153865.3-1105 / 3360428, dated May 9, 2022, 54 pages.
"Reduction of Aspiration Through Cohesive Thin Liquids (CTL) in Patients With Mild Oropharyngeal Dysphagia", U.S. National Library of Medicine, accessed at https://clinicaltrials.gov/ct2/show/NCT02522351, First Posted on Aug. 13, 2015, pp. 1-12.
Rofes, et al., "Diagnosis and Management of Oropharyngeal Dysphagia and Its Nutritional and Respiratory Complications in the Elderly", Gastroenterology Research and Practice, vol. 2011, Article ID 818979, Apr. 13, 2010, pp. 1-13.
"HAAKE CaBER 1", Instruction Manual, Version 2, 2003, 86 Pages.
Kim et al., "Capillary Breakup Extensional Rheometry of a Wormlike Micellar Solution", Korea-Australia Rheology Journal, vol. 22, Issue No. 1, 2010, pp. 31-41.
Khatun et al., "Water-Soluble Fraction of Abelmoschus esculentus L Interacts with Glucose and Metformin Hydrochloride and Alters Their Absorption Kinetics after Coadministration in Rats", International Scholarly Research Network Pharmaceutics, vol. 2011, Article ID 260537, 2011, pp. 1-5.
Chen et al., "The Determining Role of Bolus Rheology in Triggering a Swallowing", Food Hydrocolloids, vol. 25, Issue No. 3, 2011, pp. 325-332.
Fuente et al., "Rheological Aspects of Swallowing and Dysphagia: Shear and Elongational Flows", Medical Radiology Diagn Imaging, 2017, 30 Pages.
"Determination of the Extensional Relaxation Time of an Okra Water Extract," Danone Nutricia Research, Technical Report, Oct. 17, 2022, pp. 1-4.
Grounds of Appeal for European Patent Application No. 12812921.0, dated Apr. 5, 2018, 16 Pages.
"Discontinuation of the Extensional Rheometer HAAKE CaBER 1", ThermoFischer Scientific, Jun. 14, 2021, 1 Page.
Experimental Report by Dr. M. Turcanu Including Annex 1,12 Pages, Jul. 5, 2023.
European Office Action for Appl No. 12812921.0-1105 dated Aug. 4, 2023.
Petrie, "Extensional Viscosity: A Critical Discussion", Journal of Non-Newton Fluid Mechanics, vol. 137, 2006, pp. 1-21.
Sachsenheimer, "Capillary Thinning of Viscoelastic Fluid Filaments", Dec. 17, 2014, 153 Pages.
Annex 1 as Submitted in Exam Proceedings in Parent Case on Oct. 13, 2017, p. 1.

(56) References Cited

OTHER PUBLICATIONS

Summons to attend oral proceeding dated Aug. 24, 2023 for Appl No. 18153865.3-1105.

* cited by examiner

COHESIVE THIN LIQUIDS TO PROMOTE SAFE SWALLOWING IN DYSPHAGIC PATIENTS

PRIORITY CLAIMS

This application is a continuation of U.S. patent application Ser. No. 14/365,731 filed Jun. 16, 2014, which is a U.S. national stage application under 35 USC § 371 of International Appl. No. PCT/EP12/75697 filed Dec. 17, 2012, which claims priority to Provisional Patent Appl. Ser. No. 61/570,888 filed Dec. 15, 2011 and European Application No. 11193799.1 filed Dec. 15, 2011. The entire contents of the above-referenced applications are hereby expressly incorporated herein by reference.

BACKGROUND

The present disclosure is directed to nutritional products and the therapeutic use of these products. More specifically, the present disclosure is directed to nutritional products for promoting safer swallowing of food boluses for patients having swallowing conditions.

Dysphagia is the medical term for the symptom of difficulty in swallowing. Epidemiological studies estimate a prevalence rate of 16% to 22% among individuals over 50 years of age.

Esophageal dysphagia affects a large number of individuals of all ages, but is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs [e.g., sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and antireflux interventions]). It is also common for individuals with intraluminal foreign bodies to experience acute esophageal dysphagia.

Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's Disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.]), autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Dysphagia is not generally diagnosed although the disease has major consequences on patient health and healthcare costs. Individuals with more severe dysphagia generally experience a sensation of impaired passage of food from the mouth to the stomach, occurring immediately after swallowing. Among community dwelling individuals, perceived symptoms may bring patients to see a doctor. Among institutionalized individuals, health care practitioners may observe symptoms or hear comments from the patient or his/her family member suggestive of swallowing impairment and recommend the patient be evaluated by a specialist. As the general awareness of swallowing impairments is low among front-line practitioners, dysphagia often goes undiagnosed and untreated. Yet, through referral to a swallowing specialist (e.g., speech language pathologist), a patient can be clinically evaluated and dysphagia diagnosis can be determined.

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening. Furthermore, office-based assessment of dysphagia rarely occurs.

Severity of dysphagia may vary from: (i) minimal (perceived) difficulty in safely swallowing foods and liquids, (ii) an inability to swallow without significant risk for aspiration or choking, and (iii) a complete inability to swallow. Commonly, the inability to properly swallow foods and liquids may be due to food boluses being broken up into smaller fragments, which may enter the airway or leave unwanted residues in the oropharyngeal and/or esophageal tract during the swallowing process (e.g., aspiration). If enough material enters the lungs, it is possible that the patient may drown on the food/liquid that has built up in the lungs. Even small volumes of aspirated food may lead to bronchopneumonia infection, and chronic aspiration may lead to bronchiectasis and may cause some cases of asthma.

"Silent aspiration," a common condition among elderly, refers to the aspiration of the oropharyngeal contents during sleep. People may compensate for less-severe swallowing impairments by self-limiting the diet. The aging process itself, coupled with chronic diseases such as hypertension or osteoarthritis, predisposes elderly to (subclinical) dysphagia that may go undiagnosed and untreated until a clinical complication such as pneumonia, dehydration, malnutrition (and related complications) occurs. Yet, the differential diagnosis of 'aspiration pneumonia' is not necessarily indicated as a result of current care practices.

The economic costs of dysphagia are associated with hospitalization, re-hospitalization, loss of reimbursement due to pay for performance ("P4P"), infections, rehabilitation, loss of work time, clinic visits, use of pharmaceuticals, labor, care taker time, childcare costs, quality of life, increased need for skilled care. Dysphagia and aspiration impact quality of life, morbidity and mortality. Twelve-month mortality is high (45%) among individuals in institutional care who have dysphagia and aspiration. The economic burden of the clinical consequences arising from lack of diagnosis and early management of dysphagia are significant.

Pneumonia is a common clinical consequence of dysphagia. The condition often requires acute hospitalization and emergency room visits. Among those that develop pneumonia due to aspiration, the differential diagnosis of 'aspiration pneumonia' is not necessarily indicated as a result of current care practices. Based on U.S. healthcare utilization surveys from recent years, pneumonia accounted for over one million hospital discharges and an additional 392,000 were attributable to aspiration pneumonia. Individuals who have general pneumonia as the principal diagnosis have a mean 6 day hospital length of stay and incur over $18,000 in costs for hospital care. It is expected that aspiration pneumonia would carry higher costs for hospital care, based on a mean 8 day length of hospital stay. Pneumonia is life threatening among persons with dysphagia, the odds of death within 3 months is about 50% (van der Steen et al. 2002). In addition, an acute insult such as pneumonia often initiates the downward spiral in health among elderly. An insult is associated with poor intakes and inactivity, resulting in malnutrition, functional decline, and frailty. Specific interventions (e.g., to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalized individuals with neurodegenerative diseases (thus, likely to have a swallowing impairment). The conditions of Alzheimer's disease, Parkinson's disease, and multiple sclerosis account for nearly 400,000 U.S. hospital discharges annually, and up to 15% of these patients suffer dehydration. Having dehydration as the principal diagnosis is associated with a mean 4 day length of hospital stay and over $11,000 in costs for hospital care. Nevertheless, dehydration is an avoidable clinical complication of dysphagia.

Malnutrition and related complications (e.g., [urinary tract] infections, pressure ulcers, increased severity of dysphagia [need for more-restricted food options, tube feeding, and/or PEG placement and reduced quality of life], dehydration, functional decline and related consequences [falls, dementia, frailty, loss of mobility, and loss of autonomy]) can arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having a more than 3-times greater risk of infection. Infections are common in individuals with neurodegenerative diseases (thus, likely to have a chronic swallowing impairment that jeopardizes dietary adequacy). The conditions of Alzheimer's disease, Parkinson's disease, and multiple sclerosis account for nearly 400,000 U.S. hospital discharges annually, and up to 32% of these patients suffer urinary tract infection.

Malnutrition has serious implications for patient recovery. Malnourished patients have longer length of hospital stay, are more likely to be re-hospitalized, and have higher costs for hospital care. Having malnutrition as the principal diagnosis is associated with a mean 8 day length of hospital stay and nearly $22,000 in costs for hospital care. Furthermore, malnutrition leads to unintentional loss of weight and predominant loss of muscle and strength, ultimately impairing mobility and the ability to care for oneself. With the loss of functionality, caregiver burden becomes generally more severe, necessitating informal caregivers, then formal caregivers, and then institutionalization. However, malnutrition is an avoidable clinical complication of dysphagia.

Among persons with neurodegenerative conditions (e.g., Alzheimer's disease), unintentional weight loss (a marker of malnutrition) precedes cognitive decline. In addition, physical activity can help stabilize cognitive health. Thus, it is important to ensure nutritional adequacy among persons with neurodegenerative conditions to help them have the strength and endurance to participate in regular therapeutic exercise and guard against unintentional weight loss, muscle wasting, loss of physical and cognitive functionality, frailty, dementia, and progressive increase in caregiver burden.

Falls and related injuries are a special concern among elderly with neurodegenerative conditions, associated with loss of functionality. Falls are the leading cause of injury deaths among older adults. Furthermore, fall-related injuries among elderly accounted for more than 1.8M U.S. emergency room visits in a recent year. Direct medical costs totaled $179M for fatal and $19.3B for nonfatal fall-related injuries in the period of a year. As an effect of an ambitious non-payment for performance initiative introduced in U.S. hospitals in October 2008, Medicare will no longer pay hospitals for treatment cost of falls and related injuries that occur during the hospital stay. Hospitals will face a loss of about $50,000 for each elderly patient who falls and suffers hip fracture while in hospital care. This new quality initiative is based on the premise that falls are an avoidable medical error. In other words, falls are preventable within reason by applying evidence-based practices including medical nutrition therapy as nutritional interventions are efficacious in the prevention of falls and related injuries (e.g., fractures) among elderly.

Chewing and swallowing difficulties are also recognized risk factors for pressure ulcer development. Pressure ulcers are considered an avoidable medical error, preventable within reason by applying evidence-based practices (including nutritional care, as pressure ulcers are more likely when nutrition is inadequate). Pressure ulcers are a significant burden to the health care system. In U.S. hospitals in 2006, there were 322,946 cases of medical error connected with pressure ulcer development.

The average cost of healing pressure ulcers depends on the stage, ranging from about $1,100 (for stage II) to about $10,000 (for stage III & IV pressure ulcers). Thus, the estimated cost of healing the cases of medical error connected with pressure ulcer development in one year, is in the range of $323M to $3.2 B. As an effect of an ambitious non-payment for performance initiative introduced in U.S. hospitals in October 2008, Medicare will no longer pay hospitals for treatment cost of pressure ulcers that develop during the hospital stay (up to $3.2 B annually). Pressure ulcers are preventable within reason, in part, by assuring nutritional intakes are adequate. Furthermore, specific interventions including the use of specialized nutritional supplements help reduce the expected time to heal pressure ulcers once they've developed.

In U.S. long-term care facilities, quality of care standards are enforced via the frequent regulatory survey. Surveyors will consider facilities out of compliance when they uncover evidence of actual or potential harm/negative outcomes. The range of penalties include fines, forced closure, as well as lawsuits and settlement fees. The Tag F325 (nutrition) survey considers significant unplanned weight change, inadequate food/fluid intake, impairment of anticipated wound healing, failure to provide a therapeutic diet as ordered, functional decline, and fluid/electrolyte imbalance as evidence for providing sub-standard [Nutrition] care. The Tag F314 (pressure ulcers) survey mandates that the facility must ensure that a resident who is admitted without pressure ulcers does not develop pressure ulcers unless deemed unavoidable. In addition, that a resident having pressure ulcers receives necessary treatment and services to promote healing, prevent infection and prevent new pressure ulcers from developing.

Considering the prevalence of dysphagia, possible complications related thereto, and the costs associated with same, it would be beneficial to provide nutritional products that promote safer swallowing of food boluses in patients suffering from such swallowing disorders. Such nutritional products would improve the lives of a large and growing number of persons with swallowing impairments. Specific interventions (e.g., to promote oral health, help restore normal swallow, or reinforce a swallow-safe bolus) can enable persons to eat orally (vs. being tube fed and/or requiring PEG placement) and experience the psycho-social aspects of food associated with general well being while guarding against the potentially negative consequences that result from lack of adequate swallowing ability. Improvements in the intake of nutrition by dysphagic patients may also enable such patients to swallow a wider variety of food and beverage products safely and comfortably, which may lead to an overall healthier condition of the patient and prevent further health-related decline.

SUMMARY

The present disclosure is related to nutritional products and the therapeutic use of these products. More specifically, the present disclosure is related to nutritional products for promoting safer swallowing of liquids.

In a first aspect, the invention relates to a nutritional product comprising an aqueous solution of a food grade biopolymer capable of providing to the nutritional product a shear viscosity of less than about 100 mPas, preferably of less than about 50 mPas, when measured at a shear rate of 50 $s^{-1}$, and a relaxation time, determined by a Capillary Breakup Extensional Rheometry (CaBER) experiment, of more than 10 ms (milliseconds) at a temperature of 20° C.

In a preferred embodiment of the first aspect of the invention, the shear viscosity is at least about 1 mPas, preferably from at least about 1 mPas to less than about 50 mPas, and more preferably from at least 5 mPas to less than 20 mPas, when measured at a shear rate of 50 $s^{-1}$.

It is further preferred that relaxation time is less than about 2000 ms, preferably from about 20 ms to about 1000 ms, more preferably from about 50 ms to about 500 ms, and most preferably from about 100 ms to about 200 ms, at a temperature of 20° C.

In another preferred embodiment of the first aspect of the invention, the filament diameter of the nutritional product decreases less than linearly, and preferably exponentially in time during a CaBER experiment.

It is furthermore preferred that the biopolymer is comprised in the aqueous solution in a concentration of from at least 0.01 wt % to 25 wt %, preferably from at least 0.1 wt % to 15 wt %, and most preferably from at least 1 wt % to 10 wt %.

Another preferred embodiment of the first aspect of the invention relates to the nutritional product in diluted form, preferably in an aqueous dilution ranging from 2:1 to 50:1, more preferably from 3:1 to 20:1 and most preferably from 5:1 to 10:1.

In a further preferred embodiment of the first aspect of the invention, the food grade biopolymer is selected from the group consisting of botanical hydrocolloids, microbial hydrocolloids, animal hydrocolloids, algae hydrocolloids and any combination thereof.

It is particularly preferred that the algae hydrocolloids are selected from the group consisting of agar, carrageenan, alginate, or any combinations thereof. In another preferred embodiment, the microbial hydrocolloids are selected from the group consisting of xanthan gum, gellan gum, curdlan gum, or any combinations thereof. In a further preferred embodiment, the botanical hydrocolloids are selected from the group consisting of plant-extracted gums, plant-derived mucilages and combinations thereof.

The plant-extracted gums may further be selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a particularly preferred embodiment of the first aspect of the invention, the plant-extracted gum is okra gum.

The plant-derived mucilages may preferably be selected from the group consisting of kiwi fruit mucilage, cactus mucilage (*Ficus indica*), Chia seed mucilage (*Salvia hispanica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolate*), mullein mucilage (*Verbascum*), cetraria mucilage (*Lichen islandicus*), or any combinations thereof. In a particularly preferred embodiment of the first aspect of the invention, the plant-derived mucilage is kiwi fruit mucilage.

In another preferred embodiment of the first aspect of the invention, the food grade biopolymer is selected from okra gum and/or kiwi fruit mucilage, or a combination thereof. It is mostly preferred that the kiwi fruit mucilage is derived from the stem pith of kiwi fruit.

In a particularly preferred embodiment of the of the first aspect of the invention, the aqueous solution comprises rigid particles, preferably wherein the rigid particles have a size of between 1 and 100 micrometers; and/or the rigid particles are comprised in an amount of between 5 and 80 vol.-%; and/or the rigid particles are selected from the group consisting of sucrose crystals, cocoa particles, microcrystalline cellulose particles, starch and modified starch granules, protein particles, and any combination thereof.

In an embodiment of the first aspect of the invention, the nutritional products include a prebiotic. The prebiotic is preferably selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, and combinations thereof.

In another embodiment of the first aspect of the invention, the nutritional products include a probiotic. The probiotic is preferably selected from the group consisting of *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella,* and combinations thereof.

In yet another embodiment of the first aspect, the nutritional products include an amino acid. The amino acid is preferably selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, and combinations thereof.

In still yet another embodiment of the first aspect of the invention, the nutritional product preferably includes a fatty acid selected from the group consisting of docosahexaenoic acid (DHA), eicosapentaenoic acid (EPA), and combinations thereof DHA and EPA may preferably be derived from a source selected from the group consisting of fish oil, krill, plant sources containing ω-3 fatty acids, flaxseed, walnut, algae, and combinations thereof. Certain fatty acids (e.g., 18:4 fatty acids) may also be readily converted to DHA and/or EPA. The nutritional product may further include α-linolenic acid.

In an embodiment of the first aspect of the invention, the nutritional products include a phytonutrient, which is preferably selected from the group consisting of flavanoids, allied phenolic compounds, polyphenolic compounds, terpenoids, alkaloids, sulphur-containing compounds, and combinations thereof. In another preferred embodiment, the phytonutrient is selected from the group consisting of carotenoids, plant sterols, quercetin, curcumin, limonin, and combinations thereof.

In another preferred embodiment of the first aspect of the invention, the nutritional products include an antioxidant, which is preferably selected from the group consisting of astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, and combinations thereof.

In another embodiment of the first aspect of the invention, the nutritional product is in an administrable form selected from the group consisting of pharmaceutical formulations, nutritional formulations, dietary supplements, functional food and beverage products or combinations thereof.

A second aspect of the invention relates to the use of a nutritional product according to the first aspect of the invention or any of its embodiments for treating a swallowing disorder.

In a third aspect, the invention concerns the use of a nutritional product according to the first aspect of the invention or any of its embodiments for promoting safe swallowing of nutritional products in a patient in need of same.

In a fourth aspect, the invention relates to the use of a nutritional product according to the first aspect of the invention or any of its embodiments for mitigating the risks of aspiration during swallowing of nutritional products in a patient in need of same.

A fifth aspect of the invention pertains to a method for making a nutritional product, the method comprising providing an aqueous solution of a food grade biopolymer capable of providing to the nutritional product a shear viscosity of less than about 100 mPas, preferably of less than about 50 mPas, when measured at a shear rate of $50s^{-1}$, and a relaxation time, determined by a Capillary Breakup Extensional Rheometry (CaBER) experiment, of more than 10 ms (milliseconds) at a temperature of 20° C.

In a preferred embodiment of this aspect, shear viscosity is at least about 1 mPas, preferably from at least about 1 mPas to less than about 50 mPas, more preferably from at least 5 mPas to less than 20 mPas, when measured at a shear rate of $50s^{-1}$.

In another preferred embodiment of the inventive method, relaxation time is less than about 2000 ms, preferably from about 20 ms to about 1000 ms, more preferably from about 50 ms to about 500 ms, and most preferably from about 100 ms to about 200 ms.

In a particularly preferred embodiment of the fifth aspect of the invention, the filament diameter of the nutritional product decreases less than linearly, and preferably exponentially in time during a CaBER experiment.

In another preferred embodiment of the fifth aspect of the invention, the aqueous solution comprises a food grade biopolymer in a concentration of from at least 0.01 wt % to 25 wt %, preferably from at least 0.1 wt % to 15 wt %, and most preferably from at least 1 wt % to 10 wt %.

In another embodiment, the method according to the fifth aspect of the invention further comprises the step of diluting the nutritional product, preferably in an aqueous dilution ranging from 2:1 to 50:1, more preferably from 3:1 to 20:1 and most preferably from 5:1 to 10:1.

In yet another embodiment of the fifth aspect, the food grade biopolymer is selected from the group consisting of botanical hydrocolloids, microbial hydrocolloids, animal hydrocolloids, algae hydrocolloids and any combination thereof.

In still yet another embodiment of the fifth aspect of the invention, the algae hydrocolloids are selected from the group consisting of agar, carrageenan, alginate, or any combinations thereof. In another embodiment of said aspect, the microbial hydrocolloids are selected from the group consisting of xanthan gum, gellan gum, curdlan gum, or any combinations thereof. In a further embodiment of said aspect, the botanical hydrocolloids are selected from the group consisting of plant-extracted gums, plant-derived mucilages and combinations thereof.

A preferred embodiment of the invention relates to the method according to the fifth aspect, wherein the plant-extracted gums are selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In a particularly preferred embodiment thereof, the plant-extracted gum is okra gum.

Another preferred embodiment of the invention relates to the method according to the fifth aspect, wherein the plant-derived mucilages are selected from the group consisting of kiwi fruit mucilage, cactus mucilage (*Ficus indica*), Chia seed mucilage (*Salvia hispanica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. In a particularly preferred embodiment thereof, the plant-derived mucilage is kiwi fruit mucilage.

In a further preferred embodiment of the method of the invention, the food grade biopolymer is selected from okra gum and/or kiwi fruit mucilage, or a combination thereof. It is mostly preferred that in this method, the kiwi fruit mucilage is derived from the stem pith of kiwi fruit.

In a particularly preferred embodiment of the of the fifth aspect of the invention, the aqueous solution comprises rigid particles, preferably wherein the rigid particles have a size of between 1 and 100 micrometers; and/or the rigid particles are comprised in an amount of between 5 and 80 vol.-%; and/or the rigid particles are selected from the group consisting of sucrose crystals, cocoa particles, microcrystalline cellulose particles, starch and modified starch granules, protein particles, and any combination thereof.

In a further embodiment of the fifth aspect of the invention, the inventive method further comprises adding to the nutritional product a prebiotic, which is preferably selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, and combinations thereof.

In a further embodiment of the fifth aspect of the invention, the inventive method further comprises adding to the nutritional products a probiotic, which is preferably selected from the group consisting of *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, and combinations thereof.

In a further embodiment of the fifth aspect of the invention, the inventive method further comprises adding to the nutritional products an amino acid, which is preferably selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, and combinations thereof.

In a further embodiment of the fifth aspect of the invention, the inventive method further comprises adding to the nutritional product a fatty acid preferably selected from the group consisting of docosahexaenoic acid (DHA), eicosapentaenoic acid (EPA), and combinations thereof DHA and EPA may also be derived from a source selected from the group consisting of fish oil, krill, plant sources containing ω-3 fatty acids, flaxseed, walnut, algae, and combinations thereof.

Certain fatty acids (e.g., 18:4 fatty acids) may also be readily converted to DHA and/or EPA. The above method may further include adding to the nutritional product an a-linolenic acid.

In a further embodiment of the fifth aspect of the invention, the inventive method further comprises adding to the nutritional products a phytonutrient selected from the group consisting of flavanoids, allied phenolic compounds, polyphenolic compounds, terpenoids, alkaloids, sulphur-containing compounds, and combinations thereof. It is further preferred that the phytonutrient is selected from the group consisting of carotenoids, plant sterols, quercetin, curcumin, limonin, and combinations thereof.

In an embodiment, the method according to the fifth aspect of the invention further comprises adding to the nutritional product an antioxidant selected from the group consisting of astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, and combinations thereof.

In another embodiment, the method of the invention further comprises the step of bringing the nutritional products in an administrable form, which is preferably selected from the group consisting of pharmaceutical formulations, nutritional formulations, dietary supplements, functional food and beverage products or combinations thereof.

An advantage of the above aspects one to five of the invention and their embodiments is to provide improved nutritional products, and in particular to provide improved liquid nutritional products.

A particular advantage of these aspects and embodiments is to provide improved nutritional products for patients having dysphagia.

Yet another particular advantage of the above aspects and embodiments of the invention is to provide nutritional products that are useful for treating patients having dysphagia.

Yet another advantage of the above aspects and embodiments of the invention is to provide nutritional products that are useful for promoting safe swallowing of food boluses.

Additional features and advantages are described herein, and will be apparent from the following Detailed Description.

DETAILED DESCRIPTION

As used herein, "about" is understood to refer to numbers in a range of numerals. Moreover, all numerical ranges herein should be understood to include all integer, whole or fractions, within the range.

As used herein, "wt %" is understood to refer to the weight of polymer per total weight of the product.

The term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin Bi, vitamin $B_6$, vitamin $B_{12}$, vitamin C, vitamin D, vitamin E, zeaxanthin, or combinations thereof.

While the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, non-limiting examples of sources of w-3 fatty acids such a-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc.

As used herein, "food grade micro-organisms" means micro-organisms that are used and generally regarded as safe for use in food.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

As used herein, a "non-replicating" microorganism means that no viable cells and/or colony forming units can be detected by classical plating methods. Such classical plating methods are summarized in the microbiology book: James Monroe Jay, et al., *Modern food microbiology*, 7th edition, Springer Science, New York, N.Y. p. 790 (2005). Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h). For example, bifidobacteria such as *Bifidobacterium longum*, *Bifidobacterium lactis* and *Bifidobacterium breve* or *lactobacilli*, such as *Lactobacillus paracasei* or *Lactobacillus rhamnosus*, may be rendered non-replicating by heat treatment, in particular low temperature/long time heat treatment.

As used herein, a "nucleotide" is understood to be a subunit of deoxyribonucleic acid ("DNA") or ribonucleic acid ("RNA"). It is an organic compound made up of a nitrogenous base, a phosphate molecule, and a sugar molecule (deoxyribose in DNA and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5'-Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP), 5'-Inosine Monophosphate ("5'-IMP"), 5'-Thymine Monophosphate ("5'-TMP"), or combinations thereof. The exogenous nucleotide can also be in a polymeric form such as, for example, an intact RNA. There can be multiple sources of the polymeric form such as, for example, yeast RNA.

"Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein the term "patient" is understood to include an animal, especially a mammal, and more especially a human that is receiving or intended to receive treatment, as it is herein defined.

As used herein, "phytochemicals" or "phytonutrients" are non-nutritive compounds that are found in many foods. Phytochemicals are functional foods that have health benefits beyond basic nutrition, and are health promoting compounds that come from plant sources. "Phytochemicals" and "Phytonutrients" refers to any chemical produced by a plant that imparts one or more health benefit on the user. Non-limiting examples of phytochemicals and phytonutrients include those that are:

i) phenolic compounds which include monophenols (such as, for example, apiole, carnosol, carvacrol, dillapiole, rosemarinol); flavonoids (polyphenols) including flavonols (such as, for example, quercetin, fingerol, kaempferol, myricetin, rutin, isorhamnetin), flavanones (such as, for example, fesperidin, naringenin, silybin, eriodictyol), flavones (such as, for example, apigenin, tangeritin, luteolin), flavan-3-ols (such as, for example, catechins, (+)-catechin, (+)-gallocatechin, (−)-epicate chin, (−)-epigallocatechin, (−)-epigallocatechin gallate (EGCG), (−)-epicatechin 3-gallate, theaflavin, theaflavin-3 -gallate, theaflavin-3'-gallate, theaflavin-3,3'-digallate, thearubigins), anthocyanins (flavonals) and anthocyanidins (such as, for example, pelargonidin, peonidin, cyanidin, delphinidin, malvidin, petunidin), isoflavones (phytoestrogens) (such as, for example, daidzein (formononetin), genistein (biochanin A), glycitein), dihydroflavonols, chalcones, coumestans (phytoestrogens), and Coumestrol; Phenolic acids (such as: Ellagic acid, Gallic acid, Tannic acid, Vanillin, curcumin); hydroxycinnamic acids (such as, for example, caffeic acid, chlorogenic acid, cinnamic acid, ferulic acid, coumarin); lignans (phytoestrogens), silymarin, secoisolariciresinol, pinoresinol and lariciresinol); tyrosol esters (such as, for example, tyrosol, hydroxytyrosol, oleocanthal, oleuropein); stilbenoids (such as, for example, resveratrol, pterostilbene, piceatannol) and punicalagins;

ii) terpenes (isoprenoids) which include carotenoids (tetraterpenoids) including carotenes (such as, for example, α-carotene, β-carotene, γ-carotene, δ-carotene, lycopene, neurosporene, phytofluene, phytoene), and xanthophylls (such as, for example, canthaxanthin, cryptoxanthin, aeaxanthin, astaxanthin, lutein, rubixanthin); monoterpenes (such as, for example, limonene, perillyl alcohol); saponins; lipids including: phytosterols (such as, for example, campesterol, beta sitosterol, gamma sitosterol, stigmasterol), tocopherols (vitamin E), and ω-3, -6, and -9 fatty acids (such as, for example, gamma-linolenic acid); triterpenoid (such as, for example, oleanolic acid, ursolic acid, betulinic acid, moronic acid);

iii) betalains which include Betacyanins (such as: betanin, isobetanin, probetanin, neobetanin); and betaxanthins (non glycosidic versions) (such as, for example, indicaxanthin, and vulgaxanthin);

iv) organosulfides, which include, for example, dithiolthiones (isothiocyanates) (such as, for example, sulphoraphane); and thiosulphonates (allium compounds) (such as, for example, allyl methyl trisulfide, and diallyl sulfide), indoles, glucosinolates, which include, for example, indole-3-carbinol; sulforaphane; 3,3'-diindolylmethane; sinigrin; allicin; alliin; allyl isothiocyanate; piperine; syn-propanethial-S-oxide;

v) protein inhibitors, which include, for example, protease inhibitors;

vi) other organic acids which include oxalic acid, phytic acid (inositol hexaphosphate); tartaric acid; and anacardic acid; or vii) combinations thereof.

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., *Probiotics: how should they be defined?*, Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

The terms "protein," "peptide," "oligopeptides" or "polypeptide," as used herein, are understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy based proteins, plant based proteins, animal based proteins and artificial proteins. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses. Animal based proteins may be selected from the group consisting of beef, poultry, fish, lamb, seafood, or combinations thereof.

All dosage ranges contained within this application are intended to include all numbers, whole or fractions, contained within said range.

As used herein, a "symbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

The present disclosure relates to nutritional products for promoting safer swallowing of food boluses for patients suffering from swallowing disorders including, for example, dysphagia. The present disclosure also relates to methods for providing treatment for a patient having a swallowing disorder.

The normal swallowing of a human (or mammal) involves three distinct phases which are interdependent and well coordinated: (i) the oral, (ii) the pharyngeal, and (iii) the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by food/liquid bolus passing through the faucial pillars into the pharynx. Contraction of the three constrictors of the pharynx propel the bolus towards the upper esophageal sphincter. Simultaneously, the soft palate closes the nasopharynx. The larynx moves upwards to prevent food or liquid passing into the airway, which is aided by the backward tilt of the epiglottis and closure of the vocal folds. The esophageal phase is also involuntary and starts with the relaxation of the upper esophageal sphincter followed by peristalsis, which pushes the bolus down to the stomach.

Dysphagia refers to the symptom of difficulty in swallowing. The following general causes of dysphagia have been identified:
A decreased ability to swallow
Tongue not exerting enough pressure on soft palate
Iatrogenic
Surgical removal of part of the tongue or soft palate
Treatment for snoring or sleep apnea
Resection due to tumor (malignant or benign)
Genetic
Hypoplasia of the tongue and/or soft palate
Hypo or lack of innervation to tongue and/or soft palate
Traumatic
Tissue damage
Deinnervation/hypoinnervation
Neurologic
Local deinnervation/hypoinnervation
CNS
Post stroke
Demylination
Abnormal epiglottis behavior
Not closing and opening at proper times
Opening too early
Not closing in time
Delayed closing
Not closing completely (insufficient flexibility—atrophy)

The consequences of untreated or poorly managed oral pharyngeal dysphagia can be severe, including dehydration, malnutrition leading to dysfunctional immune response, and reduced functionality, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding.

Mild to moderate oral pharyngeal dysphagia may require the texture of foods to be modified in order to minimize the likelihood of choking or aspiration. This may include the thickening of liquids and/or pureeing of solid foods, both of which have been shown to be the most effective means of preventing choking and aspiration during the eating process. Thickened liquids are designed to have three properties: (i) a more cohesive bolus that can be maintained throughout the action of swallowing, (ii) slower delivery to the throat, thereby compensating for the increased period in which the swallowing reflexes prepare for the thickened liquid, and (iii) provide greater density to increase awareness of the presence of food or liquid bolus in the mouth.

Improving an individual's ability and efficiency to swallow improves the individual's safety through reduced risk of pulmonary aspiration. An efficient swallow may permit greater independence from feeding assistance and/or reduced length of time spent in feeding-assistance during meal consumption. Efficient swallowing also reduces the viscosity of liquids required for safety (e.g., pudding, honey and nectar thickness products) and may also limit the use of texture-modified foods. All of these previously described factors are aimed at improving an individual's quality of life.

Therefore, the present disclosure provides nutritional products for promoting safer swallowing of food boluses in patients with swallowing disorders (e.g., dysphagic patients)

by preventing bolus penetration and aspiration through modification of rheological properties of foods and beverages.

The nutritional products of the present invention comprise an aqueous solution of a food grade biopolymer, which is capable of providing to the nutritional product a shear viscosity of less than about 100 mPas, preferably of less than about 50 mPas, when measured at a shear rate of 50 s$^{-1}$, and a relaxation time, determined by a Capillary Breakup Extensional Rheometry (CaBER) experiment, of more than 10 ms (milliseconds) at a temperature of 20° C.

Rheology is the study of the flow of matter, primarily in the liquid state but also as soft solids or solids under conditions in which they respond with plastic flow rather than deforming elastically in response to an applied force. The flow of substances cannot generally be characterized by a single value of viscosity, although viscosity measurements at specific temperatures can provide valuable information about a material's properties. A commonly measured rheological property of a material is it's shear viscosity. Shear viscosity, often referred to as simply viscosity, describes the reaction of a material to applied shear stress. In other words, shear stress is the ratio between "stress" (force per unit area) exerted on the surface of a fluid, in the lateral or horizontal direction, to the change in velocity of the fluid as you move down in the fluid (a "velocity gradient"). In a preferred embodiment of the nutritional product of the present invention, the shear viscosity is at least about 1 mPas, preferably from at least about 1 mPas to less than about 50 mPas, and more preferably from at least 5 mPas to less than 20 mPas, when measured at a shear rate of 50 s$^{-1}$.

Another rheological property of a material is its extensional viscosity. Extensional viscosity is the ratio of the stress required to extend a liquid in its flow direction to the extension rate. Extensional viscosity coefficients are widely used for characterizing polymers, where they cannot be simply calculated or estimated from the shear viscosity. Rheological studies are generally performed using rheometers, which generally impose a specific stress field or deformation to the fluid and monitor the resultant deformation or stress. These instruments may operate in steady flow or oscillatory flow, as well as both shear and extension.

The herein used Capillary Breakup Extensional Rheometer (CaBER) is an example for a rheometer applying extensional stress. During the CaBER experiment as performed herein for measuring the relaxation time of the nutritional product, a drop of said product is placed between two vertically aligned and parallel circular metal surfaces, both having a diameter of 6 mm. The metal surfaces are then rapidly separated linearly over a time interval of 50 ms (milliseconds). The filament formed by this stretching action subsequently thins under the action of interfacial tension and the thinning process is followed quantitatively using a laser sheet measuring the filament diameter at its mid-point. The relaxation time in a CaBER experiment is determined by plotting the normalised natural logarithm of the filament diameter during the thinning process versus time and determining the slope of the linear portion (dln (D/D0)/dt) of this curve, where D is the filament diameter, D0 the filament diameter at time zero and t the time of filament thinning. The relaxation time in this context is then defined as minus one third (−⅓) times the inverse of this slope, i.e. −1/(3 dln(D/D0)/dt).

In an embodiment of the inventive nutritional product, the thus determined relaxation time is less than about 2000 ms, preferably from about 20 ms to about 1000 ms, more preferably from about 50 ms to about 500 ms, and most preferably from about 100 ms to about 200 ms, at a temperature of 20° C. It is furthermore preferred that the filament diameter of the nutritional product decreases less than linearly, and preferably exponentially in time during a CaBER experiment.

During processing in the mouth and swallowing, the viscosity of a food product changes due to shear forces. It is generally known that the viscosity of a food product decreases when the shear forces and rate acting on the food product (e.g., chewing forces) increase. A know treatment for beverages and liquid foods is to increase the viscosity of the food/beverage by adding starch or gum thickeners. Such thickening is thought to improve bolus control and timing of swallowing. It is, however, often disliked by patients because of the extra swallowing effort and may also leave residues at high levels of viscosity. For solid foods, pureed diets are often described when problems with mastication and swallowing of solid pieces occur in patients. However, these pureed diets may lack the natural cohesiveness that saliva provides to "real" food boluses.

Extensional viscosity is generally only relevant in flows where a fluid is "stretcher/extended (e.g., when a flowing through a constriction such as an esophageal sphincter), or when compressed (e.g., between the tongue and plate or the tongue and pharynx). However, any compressive force also implies an extension (e.g., in another direction). Only in so-called "simple shear" flows, like in a straight pipe would the shear viscosity alone determine the fluid flow. In a process like swallowing, most steps of the bolus transport will have a certain degree of extension as well. The difference between shear and extensional viscosity is usually expressed in terms of a "Trouton ratio," which is the ratio between the extensional viscosity and the shear viscosity at the same rate of deformation and as expressed in reciprocal seconds.

As such, and as opposed to the effects of shear viscosity, the nutritional products of the present disclosure aim to improve the cohesion of food boluses to prevent a food bolus from being broken up into smaller fragments, which may enter the airway or leave unwanted residues in the oropharyngeal and/or esophageal tract during the swallowing process. Salivary proteins appear to naturally have this function of increasing the cohesiveness of a food bolus. Applicants have surprisingly found that the incorporation of food grade biopolymers in nutritional products achieve a similar or identical, possibly even enhanced effect of increasing the cohesiveness of the food bolus (e.g., for patients who have compromised secretion of saliva). This principle may be applicable both to beverages, in which such polymers may be dissolved, and semi-solid foodstuffs (e.g., purees) which need to maintain sufficient integrity to be safely swallowed and where solid and semi-solid particles are held together by a "cohesive" aqueous phase containing such polymers.

In the nutritional product of the present invention, the aqueous solution preferably comprises such a food grade biopolymer in a concentration of from at least 0,01 wt % to 25 wt %, preferably from at least 0,1 wt % to 15 wt %, and most preferably from at least 1 wt % to 10 wt %. All percentages given in this specifications refer to the weight of polymer per total weight of the product (wt %).

Another embodiment of the present invention relates to the inventive nutritional product in diluted form, preferably in an aqueous dilution ranging from 2:1 to 50:1, more preferably from 3:1 to 20:1 and most preferably from 5:1 to 10:1. By way of example, a dilution of 2:1 means that 1 part of nutritional product is diluted in 2 parts of water.

Applicants have also found that providing nutritional products to dysphagic patients having increased bolus cohesion due to its extensional viscosity, without dramatically modifying other physical properties of the material such as, for example, its shear viscosity, dramatically reduces the amount of swallowing effort for the patient, as well as the risk of residue build-up in the oropharyngeal and/or esophageal tracts. As such, products having increased cohesiveness provide improved nutritional intake of dysphagic patients by enabling them to swallow a wider variety of food and beverage products safely and comfortably. This is achieved by improving bolus integrity ("cohesiveness") and thus lending confidence to the patient in being able to consume the different products. The nutritional improvement achieved by an improved food and water intake may lead to an overall healthier condition of the patient and prevent further decline.

The polymers included in the present nutritional products may include any high molecular weight, water-soluble biopolymer that is capable of enhancing the extensional viscosity and, thus, the cohesiveness (e.g., resistance to breakup) of the nutritional products. Such polymers may include, for example, botanical hydrocolloids, microbial hydrocolloids, animal hydrocolloids and algae hydrocolloids.

Algae hydrocolloids that may be used in the present nutritional products may include, for example, agar, carrageenan, alginate or combinations thereof. Microbial hydrocolloids that may be used in the nutritional products of the invention may be selected from xanthan gum, gellan gum, curdlan gum, or combinations thereof. The botanical hydrocolloids that may be included in the present nutritional products may be selected from plant-extracted gums, plant-derived mucilages, and combinations thereof.

Gums that may be used in the present nutritional products may include, for example, okra gum, glucomannans (konjac mannan), galactomannans (tara gum, locust bean gum, guar gum, fenugreek gum), tamarind gum, cassia gum, gum Arabic (acacia gum), gum ghatti, pectin, cellulosics, tragacanth gum, karaya gum, and combinations thereof, wherein Okra gum is preferred.

In the context of this disclosure, the gums are preferably food grade and can be commercially obtained from numerous suppliers. For example, Xanthan gum is a high molecular weight, long chain polysaccharide composed of the sugars glucose, mannose, and glucuronic acid. The backbone is similar to cellulose, with added side chains of trisaccharides. Galactomannans are polysaccharides made of a mannose backbone with (single) side chains of galactose units. The ratio of galactose to mannose differs in different galactomannans, with usually the majority being mannose. Glucomannans are polysaccharides mainly unbranched with a backbone comprised of D-glucose and D-mannose residues. Usually approximately 60% of the polysaccharide is made up of D-mannose and approximately 40% of D-glucose. In the context of the present disclosure, galactomannans and glucomannans are food grade and can be commercially obtained from numerous suppliers.

Mucilages that may be used in the present nutritional products may include, for example, kiwi fruit mucilage, cactus mucilage, chia seed mucilage, psyllium mucilage, mallow mucilage, flax seed mucilage, marshmallow mucilage, ribwort mucilage, mullein mucilage, cetraria mucilage, or combinations thereof. In a preferred embodiment of the inventive nutritional product, the food grade polymer is selected from okra gum and/or kiwi fruit mucilage, or a combination thereof.

It is particularly preferred that the plant-derived mucilage is kiwi fruit mucilage. Said mucilage is most preferably derived from the stem pith of kiwi fruit. The stem of kiwi fruit, which typically represents the plant waste material remaining from kiwi fruit agriculture, contains about 20% of mucilage.

In the context of this disclosure, also the mucilages are preferably food grade and can be commercially obtained from numerous suppliers.

Moreover, according to the present invention, the gums and mucilages may be obtained by any suitable extraction method known in the art. A general protocol for extracting gums and mucilages involves soaking the raw plant material with 10 times of its weight of distilled water and keeping it overnight. A viscous solution is obtained, which is passed through a muslin cloth. The gum or mucilage is precipitated by addition of 95% by weight of ethanol in a ratio of about 1:1 by continuous stirring. A coagulated mass is obtained, which is subsequently dried in an oven at 40 to 45° C., powdered by passing through a sieve and stored in an airtight container.

In the nutritional product of the invention, it is further preferred that the above specified aqueous solution of a food grade biopolymer further comprises rigid particles. In the context of this disclosure, the term "rigid" means that the particles show no measurable deformation under the forces encountered during swallowing. Such particles may preferably be selected from sucrose crystals, cocoa particles, microcrystalline cellulose particles, starch and modified starch granules, protein particles, and any combination thereof.

The thus defined rigid particles may have a size of between 1 and 100 micrometers, more preferably between 1.5 and 80 micrometers, and most preferably between 2 and 50 micrometers.

In the present invention, the particle size is expressed in terms of the average equivalent particle diameter. In the context of this disclosure, the equivalent particle diameter refers to the diameter of a sphere of equal volume as the particle volume, which may be determined by any suitable method known in the art. Preferably, the equivalent particle diameter is determined by laser diffraction, e.g. using a Malvern® Mastersizer instrument. Further, in this context, the average equivalent particle diameter is based on a number average, which is to be understood as the arithmetic mean of all particle diameters in a sample, usually reported as $D[1,0]$.

Moreover, it is particularly preferred that the rigid particles have an elongated shape, which means that they have an aspect ratio of larger than 1.0.

It is further preferred that the above rigid particles are comprised in the aqueous solution of a food grade biopolymer in an amount of between 5 and 80 vol.-%, more preferably between 10 and 70 vol.-%, and most preferably between 15 and 50 vol.-%. In the context of this disclosure, vol.-% signifies the percentage of the volume of all rigid particles in the solution as a whole, per total volume of said solution.

The presence of such rigid particles in the nutritional product of the invention was found to locally enhance extensional flow and to thereby increase extensional stresses, leading to a higher apparent extensional viscosity of said product.

The nutritional products of the invention may further comprise high molecular weight proteins that may include, for example, collagen-derived proteins such as gelatin, plant proteins such as potato, pea, lupin, etc., or other proteins of sufficiently high molecular weight (MW=100 kDa and above).

In a preferred embodiment, the nutritional product of the invention may comprise a source of dietary protein including, but not limited to animal protein (such as meat protein or egg protein), dairy protein (such as casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate)), vegetable protein (such as soy protein, wheat protein, rice protein, and pea protein), or combinations thereof. In an embodiment, the protein source is selected from the group consisting of whey, chicken, corn, caseinate, wheat, flax, soy, carob, pea, or combinations thereof.

In another embodiment, the nutritional products of the invention may comprise a source of carbohydrates. Any suitable carbohydrate may be used in the present nutritional products including, but not limited to, sucrose, lactose, glucose, fructose, corn syrup solids, maltodextrin, modified starch, amylose starch, tapioca starch, corn starch or combinations thereof.

In another embodiment of the invention, the nutritional products include a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like), animal fats (such as milk fat) or combinations thereof.

In a preferred embodiment of the invention, the nutritional products further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

In another preferred embodiment of the invention, the nutritional products further include one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

Moreover, preferably, one or more amino acids may also be present in the inventive nutritional products. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

In further embodiments, the nutritional products further include one or more synbiotics, sources of ω-3 fatty acids, and/or phytonutrients. As used herein, a synbiotic is a supplement that contains both a prebiotic and a probiotic that work together to improve the microflora of the intestine.

Non-limiting examples of sources of ω-3 fatty acids such α-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc. Non-limiting examples of phytonutrients include quercetin, curcumin and limonin and combinations thereof.

According to the invention, one or more antioxidants may also be present in the nutritional products. Non-limiting examples of antioxidants include carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

The nutritional products may also include fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

The nutritional products of the invention may also include other functional ingredients including chitosans and protein aggregates. Chitosans are linear polysaccharides composed of randomly distributed β-(1-4)-linked D-glucosamine (deacetylated unit) and N-acetyl-D-glucosame (acetylated unit). Among other potential benefits, chitosans have natural antibacterial properties, aid in drug delivery, and are known to rapidly clot blood. Protein aggregates are coalescences of miss-folded proteins driven by interactions between solvent-exposed hydrophobic surfaces that are normally buried within a protein's interior.

Another aspect of the invention relates to methods for making the above nutritional product. The methods include providing a solution of a food grade biopolymer capable of providing to the nutritional product a shear viscosity of less than about 100 mPas, preferably of less than about 50 mPas, when measured at a shear rate of 50 $s^{-1}$, and a relaxation time, determined by a Capillary Breakup Extensional Rheometry (CaBER) experiment, of more than 10 ms (milliseconds) at a temperature of 20° C. In an embodiment, shear viscosity is at least about 1 mPas, preferably from at least about 1 mPas to less than about 50 mPas, more preferably from at least 5 mPas to less than 20 mPas, when measured at a shear rate of 50 $s^{-1}$. In a preferred embodiment of the inventive method, relaxation time is less than about 2000 ms, preferably from about 20 ms to about 1000 ms, more preferably from about 50 ms to about 500 ms, and most preferably from about 100 ms to about 200 ms. In another preferred embodiment, the filament diameter of the nutritional product decreases less than linearly, and preferably exponentially in time during a CaBER experiment. In yet another preferred embodiment, the aqueous solution comprises a food grade biopolymer in a concentration of from at least 0.01 wt % to 25 wt %, preferably from at least 0.1 wt % to 15 wt %, and most preferably from at least 1 wt % to 10 wt %. In a further embodiment, the method includes further diluting the nutritional product, preferably in an aqueous dilution ranging from 2:1 to 50:1, more preferably from 3:1 to 20:1 and most preferably from 5:1 to 10:1.

In yet another aspect of the invention, a method for improving the cohesiveness of a nutritional product is provided. This method includes adding to a nutritional product a solution of a food grade biopolymer capable of providing to the nutritional product a shear viscosity of less than about 100 mPas, preferably of less than about 50 mPas, when measured at a shear rate of 50 $s^{-1}$, and a relaxation time, determined by a Capillary Breakup Extensional Rheometry (CaBER) experiment, of more than 10 ms (milliseconds) at a temperature of 20° C., such that the nutritional product does not break-up during consumption of the nutritional product. Preferably, shear viscosity is at least about 1 mPas, more preferably from at least about 1 mPas to less than about 50 mPas, and most preferably from at least 5 mPas to less than 20 mPas, when measured at a shear rate of 50 s$^{-1}$. It is also preferred that relaxation time is less than about 2000 ms, more preferably from about 20 ms to about 1000 ms, even more preferably from about 50 ms to about 500 ms, and most preferably from about 100 ms to about 200 ms. In another preferred embodiment of this aspect of the invention, the filament diameter of the nutritional product decreases less than linearly, and preferably exponentially in time during a CaBER experiment. In yet another preferred embodiment, the aqueous solution comprises a food grade biopolymer in a concentration of from at least 0.01 wt % to 25 wt %, preferably from at least 0.1 wt % to 15 wt %, and most preferably from at least 1 wt % to 10 wt %. In a further preferred embodiment, the nutritional product is further diluted, preferably in an aqueous dilution ranging from 2:1 to 50:1, more preferably from 3:1 to 20:1 and most preferably from 5:1 to 10:1.

The present invention further provides methods for promoting safe swallowing of food boluses. These methods include adding to a nutritional product a solution of a food grade biopolymer capable of providing to the nutritional product a shear viscosity of less than about 100 mPas, preferably of less than about 50 mPas, when measured at a shear rate of 50 s$^{-1}$, and a relaxation time, determined by a Capillary Breakup Extensional Rheometry (CaBER) experiment, of more than 10 ms (milliseconds) at a temperature of 20° C., such that the nutritional product does not break-up during consumption of the nutritional product. Preferably, shear viscosity is at least about 1 mPas, more preferably from at least about 1 mPas to less than about 50 mPas, and most preferably from at least 5 mPas to less than 20 mPas, when measured at a shear rate of 50 s$^{-1}$. It is also preferred that relaxation time is less than about 2000 ms, more preferably from about 20 ms to about 1000 ms, even more preferably from about 50 ms to about 500 ms, and most preferably from about 100 ms to about 200 ms. In another preferred embodiment of this aspect of the invention, the filament diameter of the nutritional product decreases less than linearly, and preferably exponentially in time during a CaBER experiment. In yet another preferred embodiment, the aqueous solution comprises a food grade biopolymer in a concentration of from at least 0.01 wt % to 25 wt %, preferably from at least 0.1 wt % to 15 wt %, and most preferably from at least 1 wt % to 10 wt %. In a further preferred embodiment, the nutritional product is further diluted, preferably in an aqueous dilution ranging from 2:1 to 50:1, more preferably from 3:1 to 20:1 and most preferably from 5:1 to 10:1.

In yet another aspect of the invention, methods for treating a patient having a swallowing disorder are provided. These methods include administering to a patient in need of same a nutritional product comprising an aqueous solution of a food grade biopolymer capable of providing to the nutritional product a shear viscosity of less than about 100 mPas, preferably of less than about 50 mPas, when measured at a shear rate of 50 s$^{-1}$, and a relaxation time, determined by a Capillary Breakup Extensional Rheometry (CaBER) experiment, of more than 10 ms (milliseconds) at a temperature of 20° C., such that the nutritional product does not break-up during consumption of the nutritional product. Preferably, shear viscosity is at least about 1 mPas, more preferably from at least about 1 mPas to less than about 50 mPas, and most preferably from at least 5 mPas to less than 20 mPas, when measured at a shear rate of 50 s$^{-1}$. It is also preferred that relaxation time is less than about 2000 ms, more preferably from about 20 ms to about 1000 ms, even more preferably from about 50 ms to about 500 ms, and most preferably from about 100 ms to about 200 ms. In another preferred embodiment of this aspect of the invention, the filament diameter of the nutritional product decreases less than linearly, and preferably exponentially in time during a CaBER experiment. In yet another preferred embodiment, the aqueous solution comprises a food grade biopolymer in a concentration of from at least 0.01 wt % to 25 wt %, preferably from at least 0.1 wt % to 15 wt %, and most preferably from at least 1 wt % to 10 wt %. In a further preferred embodiment, the nutritional product is further diluted, preferably in an aqueous dilution ranging from 2:1 to 50:1, more preferably from 3:1 to 20:1 and most preferably from 5:1 to 10:1.

It is particularly preferred in any one of the above methods that the food grade biopolymer is selected from the group consisting of botanical hydrocolloids, microbial hydrocolloids, animal hydrocolloids, algae hydrocolloids and any combination thereof.

It is further preferred that the algae hydrocolloids are selected from the group consisting of agar, carrageenan, alginate, or any combinations thereof. Moreover, the microbial hydrocolloids are preferably selected from the group consisting of xanthan gum, gellan gum, curdlan gum, or any combinations thereof. Furthermore, the botanical hydrocolloids are preferably selected from the group consisting of plant-extracted gums, plant-derived mucilages and combinations thereof.

In any one of the above methods of the invention, the plant-extracted gums may preferably be selected from the group consisting of okra gum, konjac mannan, tara gum, locust bean gum, guar gum, fenugreek gum, tamarind gum, cassia gum, acacia gum, gum ghatti, pectins, cellulosics, tragacanth gum, karaya gum, or any combinations thereof. In preferred embodiments, the plant-extracted gum is okra gum. Further, the plant-derived mucilages may preferably be selected from the group consisting of kiwi fruit mucilage, cactus mucilage (*Ficus indica*), chic seed mucilage (*Salvia hispanica*), psyllium mucilage (*Plantago ovata*), mallow mucilage (*Malva sylvestris*), flax seed mucilage (*Linum usitatissimum*), marshmallow mucilage (*Althaea officinalis*), ribwort mucilage (*Plantago lanceolata*), mullein mucilage (*Verbascum*), cetraria mucilage (*Lichen islandicus*), or any combinations thereof. It is mostly preferred that the plant-derived mucilage is kiwi fruit mucilage, which is most preferably derived from the stem pith of kiwi fruit.

In preferred embodiments of the above referenced methods, the food grade biopolymer is selected from okra gum and/or kiwi fruit mucilage, or a combination thereof.

In any one of the above methods of the invention, it is particularly preferred that the aqueous solution of a food grade biopolymer further comprises rigid particles. Such particles may preferably be selected from sucrose crystals, cocoa particles, microcrystalline cellulose particles, starch and modified starch granules, protein particles, and any combination thereof.

Moreover, these rigid particles may have a size of between 1 and 100 micrometers, more preferably between 2.5 and 80 micrometers, and most preferably between 5 and 50 micrometers. It is particularly preferred that the rigid particles are elongated, which means that they have an aspect ratio of larger than 1.0.

It is further preferred that the thus defined rigid particles are added to the aqueous solution of a food grade biopolymer according to the invention in an amount of between 5 and 80 vol.-%, more preferably between 10 and 70 vol.-%, and most preferably between 15 and 50 vol.-%. In the context of this disclosure, vol.-% signifies the percentage of the volume of all rigid particles in the solution as a whole, per total volume of said solution.

In the above methods of the invention it is further preferred that the nutritional product comprises a source of dietary protein including, but not limited to animal protein (such as meat protein or egg protein), dairy protein (such as casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate)), vegetable protein (such as soy protein, wheat protein, rice protein, and pea protein), or combinations thereof. In an embodiment, the protein source is selected from the group consisting of whey, chicken, corn, caseinate, wheat, flax, soy, carob, pea, or combinations thereof.

In the above methods of the invention it is also preferred that the nutritional product comprises a source of carbohydrates. Any suitable carbohydrate may be used in the present nutritional products including, but not limited to, sucrose, lactose, glucose, fructose, corn syrup solids, maltodextrin, modified starch, amylose starch, tapioca starch, corn starch or combinations thereof.

The nutritional products may further include a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like), animal fats (such as milk fat) or combinations thereof.

In preferred embodiments of the above methods according to the invention, the nutritional products further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

In further preferred embodiments of the above methods according to the invention, the nutritional products further include one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

Moreover, preferably, one or more amino acids may also be present in the inventive nutritional products. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

In further embodiments of the inventive methods, the nutritional products further include one or more synbiotics, sources of ω-3 fatty acids, and/or phytonutrients. As used herein, a synbiotic is a supplement that contains both a prebiotic and a probiotic that work together to improve the microflora of the intestine. Non-limiting examples of sources of (ω-3 fatty acids such α-linolenic acid ("ALA"), docosahexaenoic acid ("DHA") and eicosapentaenoic acid ("EPA") include fish oil, krill, poultry, eggs, or other plant or nut sources such as flax seed, walnuts, almonds, algae, modified plants, etc. Non-limiting examples of phytonutrients include quercetin, curcumin and limonin and combinations thereof.

In further preferred embodiments of the above methods according to the invention, one or more antioxidants may also be present in the nutritional products. Non-limiting examples of antioxidants include carotenoids, coenzyme Q10 ("Co Q10"), flavono ids, glutathione Goji (wolfberry), hesperidin, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

In these methods, the nutritional products may also include fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

In other embodiments of the above methods, the nutritional products of the invention may also include other functional ingredients including chitosans and protein aggregates.

By using the improved nutritional products and methods of making and administering same, the nutritional intake of dysphagic patients may be improved by enabling them to swallow a wider variety of food and beverage products safely and comfortably. Such advantages may be achieved by improving the cohesiveness of a food bolus, which lends to the confidence of the patient in being able to consume a variety of products without the food bolus breaking up and possibly being aspirated by the patient. Such nutritional improvements may lead to an overall healthier condition of the patient and prevent further health-related decline.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating an individual having a swallowing disorder, the method comprising:
    administering an effective amount of a liquid nutritional product to the individual having the swallowing disorder, the liquid nutritional product comprising a nutritional composition and a plant-derived mucilage selected from the group consisting of kiwi fruit mucilage, mallow mucilage, ribwort mucilage, mullein mucilage, and mixtures thereof, the liquid nutritional product comprises an amount of the plant-derived mucilage such that the liquid nutritional product has an increased cohesiveness relative to the nutritional composition, has a shear viscosity less than about 100 mPas when measured at a shear rate of $50s^{-1}$ and has a relaxation time, determined by a Capillary Breakup Extensional Rheometry (CaBER) experiment, more than 10 milliseconds at a temperature of 20° C.

2. The method of claim 1, wherein the shear viscosity of the liquid nutritional product is 5 mPas to 20 mPas when measured at a shear rate of $50s^{-1}$.

3. The method of claim 1, wherein the relaxation time of the liquid nutritional product is about 100 milliseconds to about 200 milliseconds.

4. The method of claim 1, wherein the swallowing disorder is at least one of dysphagia or compromised saliva excretion.

5. The method of claim 1, wherein the liquid nutritional product has a form selected from the group consisting of pharmaceutical formulations, nutritional formulations, dietary supplements, functional food and beverage products, and combinations thereof.

6. The method of claim 1, wherein the liquid nutritional product further comprises an additional ingredient selected from the group consisting of a probiotic, a prebiotic, an amino acid, a fatty acid, a phytonutrient, an antioxidant, and mixtures thereof.

7. The method of claim 1, wherein the plant-derived mucilage comprises kiwi fruit mucilage.

\* \* \* \* \*